United States Patent [19]

Finney

[11] Patent Number: 4,611,584

[45] Date of Patent: Sep. 16, 1986

[54] EXPANDABLE PENILE IMPLANT

[75] Inventor: Roy P. Finney, Tampa, Fla.

[73] Assignee: Medical Engineering Corp., Racine, Wis.

[21] Appl. No.: 606,332

[22] Filed: May 2, 1984

Related U.S. Application Data

[63] Continuation-in-part of Ser. No. 150,231, May 15, 1980, Pat. No. 4,318,396, and a continuation-in-part of Ser. No. 266,455, May 22, 1981, abandoned, and a continuation-in-part of Ser. No. 328,827, Dec. 9, 1981, Pat. No. 4,411,261, and a continuation-in-part of Ser. No. 478,449, Mar. 24, 1983, Pat. No. 4,532,920.

[51] Int. Cl.⁴ ............................................. A61F 5/00
[52] U.S. Cl. ......................................... 128/79; 623/12
[58] Field of Search .................... 128/79; 3/1; 623/11, 623/12

[56] References Cited

U.S. PATENT DOCUMENTS

| | | | |
|---|---|---|---|
| 3,893,456 | 7/1975 | Small et al. | 128/79 |
| 4,041,948 | 8/1977 | Flam et al. | 604/369 |
| 4,066,073 | 1/1978 | Finney et al. | 128/79 |
| 4,157,085 | 6/1979 | Austad | 128/1 R |
| 4,201,202 | 5/1980 | Finney et al. | 128/79 |
| 4,204,530 | 5/1980 | Finney | 128/79 |
| 4,335,714 | 6/1982 | Edgerton | 128/79 |
| 4,424,305 | 1/1984 | Gould et al. | 525/127 |

OTHER PUBLICATIONS

Page 530 from The Journal of Urology entitled "The Effect of Hydron on Latex Urinary Catheters".

*Primary Examiner*—Stephen C. Pellegrino
*Attorney, Agent, or Firm*—Quarles & Brady

[57] ABSTRACT

A penile implant for use in treating erectile impotence includes an elongated flexible rod having a short proximal stem to support the implant and longer distal portion to be implanted in the corpus cavernosum of a penis. A layer of swellable hydrophilic material covers at least part of the distal portion. When the implant is implanted, the hydrophilic layer absorbs water and expands to increase the girth of the penis.

5 Claims, 6 Drawing Figures

EXPANDABLE PENILE IMPLANT

RELATED APPLICATIONS

This application is a continuation-in-part of my earlier applications Ser. No. 150,231 filed May 15, 1980, now U.S. Pat. No. 4,318,396, Ser. No. 5,266,455 filed May 22, 1981 now abandoned, Ser. No. 328,827 filed Dec. 9, 1981, now U.S. Pat. No. 4,411,261, and Ser. No. 478,449 filed Mar. 24, 1983 now U.S. Pat. No. 4,532,920.

FIELD OF THE INVENTION

The present invention relates to a novel penile implant which can be used in the treatment of erectile impotence. More particularly, it relates to an improved rod-type penile implant.

BACKGROUND OF THE INVENTION

There are instances of erectile impotence in which the patient does not respond to more conventional therapy, and the surgical implanting of a penile prosthesis is the only practical means of remedying the impotency.

In the past, several types of implantable penile prostheses have been employed. The first and most common type is a pair of identical rods of suitable stiffness. Each of the rods is surgically implanted into a corpus cavernosum of the penis. The implants disclosed in U.S. Pat. Nos. 3,853,122 and 4,066,073 are representative of this type of penile prosthesis.

Another type of penile prosthesis which is available is the inflatable prosthesis. The most common inflatable prosthesis includes a pair of fairly long inflatable and expandable tubes. Each of the tubes is surgically implanted in a corpus cavernosum of the penis. The two tubes are connected by tubing to a pressure bulb of inflating fluid which is implanted elsewhere in the body. Because of the volume required to pressurize, inflate and expand the inflatable tubes, the pressure bulbs are relatively large. For example, in U.S. Pat. No. 3,954,102, an inflatable prosthesis is disclosed in which the fluid is supplied from a single relatively large reservoir which is implanted in the abdominal cavity. The prosthesis of U.S. Pat. No. 4,009,711 includes two implants each having its own relatively large pressurizing bulb which is surgically implanted in the scrotal sac.

The inflatable type implant has an advantage over the rod-type implant in that its size can be increased to provide a more natural erection. On the other hand, the rod-type implant is more dependable as the inflatable type can develop leaks.

In U.S. Pat. No. 4,201,202 a novel implant is disclosed which is a combination rod-type and inflatable prosthesis. The prosthesis consists of a pair of rod implants, preferably of the type disclosed in U.S. Pat. No. 4,066,073, which have been provided with a flexible sleeve positioned and sealed axially about an intermediate portion of the rod to form a chamber for pressurizing fluid. The implants also each have a pressure bulb of pressurizing fluid connected by tubing to the chamber is that it can be pressurized and a valve to depressurize the chamber. An erection of the penis can be achieved with the patented implant by pressurizing the chambers if a soft rod is used or by manually moving the implants to an erect position if a stiffer hinged rod is used. The implant has an advantage over the conventional rod implant in that it can be pressurized to increase its girth.

SUMMARY OF THE INVENTION

It is the general object of the present invention to disclose an improved rod-type penile implant which increases in girth after implantation.

The ideal penile implant is one that results in the penis being as large as the normal erect penis in both length and diameter. Most penile implants are done on men who are 55 years old or older and they not infrequently have fibrosis of the erectile tissues inside the corpora cavernosa. The fibrotic tissue often cannot be dilated enough to allow a large diameter implant (12-13 mm) to be inserted. Many times a 9 or 10.5 mm diameter implant is the maximum which can be used. This leaves a penis which is rigid but which has a girth far less than the penis had when it could become erect normally.

The implant of the present invention permits the largest diameter implant which will fit the dilated space to be implanted. After it is in place the implant gradually expands in girth, exerts pressure on the fibrotic tissue and gradually dilates or stretches the tissue until the penis approaches a more normal erect girth.

The penile implant of the present invention includes an elongated, flexible rod having a short, proximal portion of relatively stiff material which is adapted to be implanted into the root end of the corpus cavernosum to support the implant and a longer distal portion preferably of a softer and less stiff material which is adapted to be implanted in the corpus cavernosum of the pendulous penis. At least a section of the distal portion of said rod is covered with an outer layer of a swellable hydrophilic material.

The implant of the present invention also differs structurally from that of U.S. Pat. No. 4,201,202 in that it has no pressure bulb or connective tubing. As a result, the entire implant can be implanted within the corpus cavernosum of the penis without the need for additional surgery.

The hydrophilic layer of the implant of the present invention once implanted absorbs water from the surrounding body fluids and tissue and increases in size thereby gradually stretching the tissue of the penis and increasing its girth. In one embodiment of the invention, the layer is a coating of hydrophilic material applied directly to a distal portion of the rod and in another embodiment the layer of swellable hydrophilic material, which could be a hypertonic liquid or a hydroscopic powder, is contained within a chamber formed between the rod and a protective outer cover of biocompatible material, such as a medical grade silicone rubber, which allows the free passage of water molecules.

DESCRIPTION OF THE PREFERRED EMBODIMENT

Figure 1:
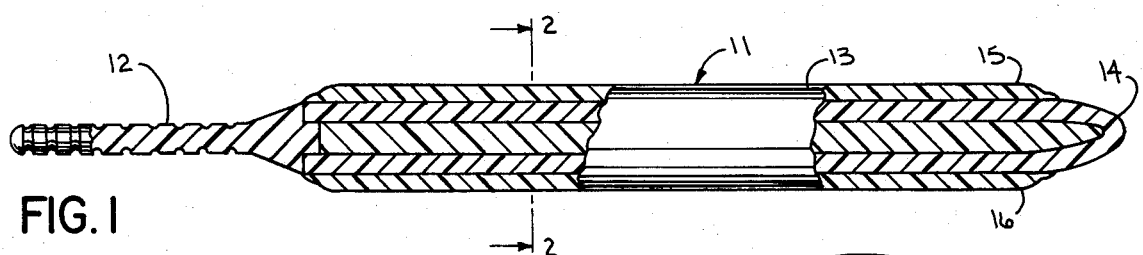
FIG. 1 is a side view, partly in section, of one embodiment of the penile implant of the present invention prior to implantation.

As seen in FIGS. 1-4, the penile implant comprises an elongated rod 11 of a physiologically inert or biocompatible material such as medical grade silicone rubber. The rod 11 has a short, proximal portion 12 of relatively stiff material which is to be implanted in the root end of the corpus cavernosum to support and anchor the implant, and a longer distal portion 13 of a softer, more flexible material which is to be implanted into the corpus cavernosum of the pendulous penis. The distal portion 13 has a tip 14 which is paraboloidal to conform in shape to the inner end of the corpus cavernosum of the penis. The distal portion 13 is covered with an outer layer 15 of swellable hydrophilic material 16.

Figure 3:
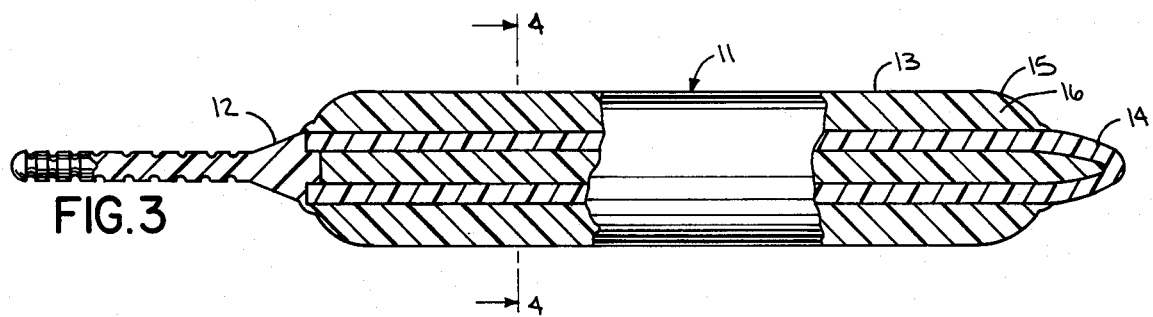
FIG. 3 is a view similar to FIG. 1, showing the implant after implantation and with the hydrophilic layer swollen.

In FIG. 1 the implant is seen in the state in which it would be implanted. The layer 15 of the hydrophilic material 16 is not swollen. In FIG. 3 the implant is seen in the state it assumes after it has been implanted long enough for the layer 15 of hydrophilic material 16 to absorb water from the body.

Figure 2:
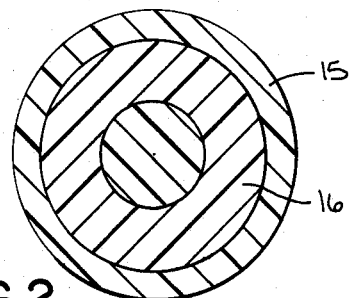
FIG. 2 is a cross sectional view taken along the lines 2—2 of FIG. 1.
Figure 4:
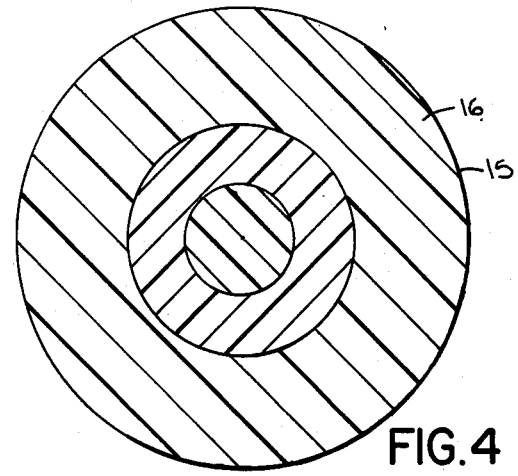
FIG. 4 is a view taken along line 4—4 in FIG. 3.

Referring now to FIGS. 2 and 4, it can be seen that the layer 15 of hydrophilic material 16 has increased in diameter after implanting and has caused the overall girth of the implant to increase.

Although in the drawings a single penile implant is shown, as previously described, a complete penile prosthesis will normally include two separate penile implants each of which is surgically implanted in a separate corpus cavernosum of a penis.

When implanted the proximal stem portion 12 of the penile implant is positioned in the root end of the corpus cavernosum to anchor the implant, and the paraboloidal tip 14 is positioned in the glans end of the corpus cavernosum. As a result, the implants are at all times positioned correctly in the corpra cavernosum of the penis and the likelihood of displacement is minimized.

Once implanted the hydrophilic material 16 absorbs water from tissue and swells to increase the girth of the penis. If the swelling is not proceeding quickly enough, sterile distilled water can be injected directly into the hydrophilic material 16 of the implants individually through a hollow needle which is connected to a syringe (not shown). The needle is inserted through the glans of the penis and into the hydrophilic material 16.

Figure 5:
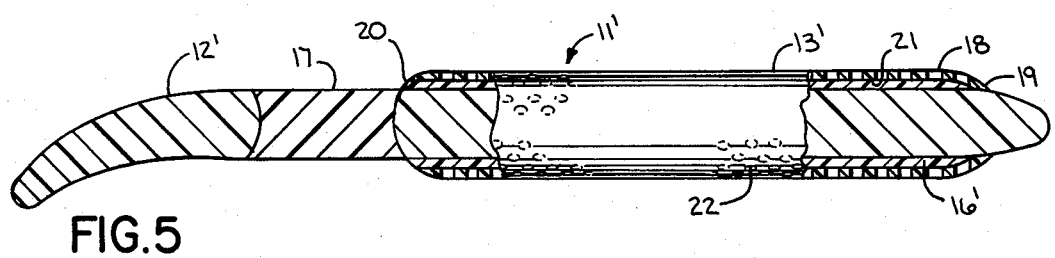
FIG. 5 is a side view, like FIG. 1, of another embodiment of the penile implant of the present invention.

In the second embodiment of the invention seen in FIG. 5, the rod 11' has the distal portion 13' and the proximal portion 12' joined by a hinge 17 as in the rod of U.S. Pat. No. 4,066,073. Positioned about the distal portion 13' is an outer cover 18 which is sealed at its respective ends 19 and 20 to the rod 11' to form a chamber 21 which contains the hydrophilic material 16'. The seals between the cover ends 19 and 20 and the adjacent areas of the rod 11' are preferably made with a suitable silicone adhesive. As seen in FIG. 5 the cover 18 has a plurality of openings 22 which expose the hydrophilic material to body tissue from which it can absorb the water necessary to swell.

The two described embodiments of the invention can be used where the hydrophilic material is one of proven biocompatibility and and where there is no danger that it will migrate from the desired location. If it is desired to use a hydrophilic material which might migrate from the chamber or which is not of proven biocompatibility the cover 18 may be formed of an imperforate membrane which is water permeable.

The rod of the implant obviously may take other forms than those described. However, the rod should be stiff enough so that it will be capable of providing the patient with a usable erection. Therefore, the word "rod" as used in the specification and claims is intended to cover any structure functionally equivalent to those described for purposes of illustration.

In the foregoing description, the proximal portions of the rods have been described as being stiff whereas the distal portions have been described as being relatively flexible. While the term "stiff" has been used to describe the desired physical properties of the material of the rod, a more precise and technical term is flexural modulus, which is the ratio of applied force to resulting deflection. However, most tables of properties do not describe the stiffness properties of rubber or rubberlike material. However, they do list related properties such as hardness.

Hardness is measured by a durometer such as a Shore A durometer which ascertains the depth of penetration of a specific indentor into a specimen under specified conditions. A scale is chosen so that 9 represents a material showing no measurable resistance to indentation and 100 represents a material showing no measurable indentation.

In the preferred embodiment of the invention, the proximal portion of the rod has a Shore hardness of about 70, the distal portion has a Shore hardness of about 20, and the material has sufficient tensile strength for its intende d use. Although materials of the described characteristics are preferred, any material which performs satisfactory under conditions of use can be employed.

Figure 6:
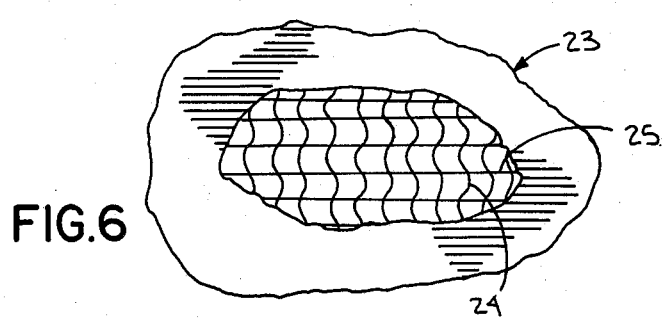
FIG. 6 is an enlarged view of a limited expansion sleeve fabric which can be used with the implant of FIG. 5.

The cover 18 preferably is made of an elastomer which will expand as the hydrophilic material 16' swells thus allowing the penis to become larger. However, if desired, the material may be an elastomer coated fabric which will expand to only a limited predetermined extent. A sample of a coated woven fabric 23 is shown in FIG. 6. As seen in the drawing, the axial threads 24 of the fabric are normally crimped and the longitudinally extending threads 25 are straight. A silicone coated fabric of this design will expand to only a limited extent axially.

The preferred hydrophilic materials are the polymeric gel HYDRON or a swellable hydrophilic gel of the type disclosed in U.S. Pat. Nos. 4,424,305; 4,138,382; 4,337,327; 4,331,783 and 4,379,874, which are incorporated by reference herein. The hydrophilic material may also take the form of a hydroscopic powder or a hypertonic liquid in which cases an imperforate outer cover 18 will have to be employed.

The preferred method of implantation of implant is through the perineum. After appropriate incision, the corpus cavernosum is dilated distally and proximally to accept the implant. The appropriate anatomical measurements are made to insure that the proximal portion of implant will be positioned at the base of the penis below the pelvic bone. An implant having an appropriately sized distal portion is obtained and the distal portion inserted into the corpus cavernosum of the penis with the tip positioned in the distal end of the corpus cavernosum. The proximal portion of implant may then be cut to the appropriate length.

During the manufacture of implant the length of proximal portion may be deliberately made longer than necessary thereby permitting it to be trimmed to the correct length at the time of surgery. Only one implant of each distal portion length need, therefore, be available since other anatomical length variations may be accommodated by trimming proximal portion. This greatly reduces the number of implant sizes which must be produced over that which would be required if no such size alteration were possible. The proximal portion is inserted in the dilated crus after trimming. The incision is then closed. The identical procedure is performed on the other side of the penis to complete the surgical procedure. The distal portions of the two implants may diverge laterally to accommodate the anatomy and provide lateral stability to the penis.

Once the implants have been implanted the hydrophilic material will absorb water over an extended period of time and swell to gradually stretch the tunica albugenia of the corpora and tissue of the penis to accept the increased girth of the implants.

It will be readily apparent to those skilled in the art that a variety of changes and modifications might be made without departing from the spirit and scope of the invention. Therefore, the scope of the invention is not to be limited except by the claims which follow.

I claim:

1. A penile implant which is readily implanted and which grows in girth after implanting, said penile implant comprising:
   (a) an elongated rod of physiologically inert material having a relatively short proximal stem portion adapted to be inserted into the root end of the corpus cavernosum of a penis, and a longer distal portion with a tip adapted to be implanted in the corpus cavernosum of the pendulous penis;
   (b) a layer of hydrophilic material which swells as it absorbs water covering and surrounding a section of said rod; and
   (c) a water permeable outer cover protecting said layer of hydrophilic material, said cover being of a material which will expand to only a limited extent when the layer of hydrophilic material absorbs water and swells.

2. A penile implant of claim 1 in which the water permeable cover contains a plurality of openings.

3. The implant of claim 1 in which the cover is formed of a silicone coated fabric which has axial threads that are crimped when the chamber is not expaned and the degree of axial expansion of the cover is limited to that afforded by the straightening of the axial threads.

4. A rod-type penile implant which expands after implanting to increase the girth of a penis in which it is implanted, said implant comprising:
   (a) an elongated rod of physiologically inert material having a relatively short proximal stem portion adapted to be inserted into the root end of the corpus cavernosum of a penis, and a longer distal portion with a tip adapted to be implanted in the corpus cavernosum of the pendulous penis;
   (b) a water permeable cover positioned about a section of the distal portion of said rod and sealed at each end of the rod to form an elongated chamber; and
   (c) a swellable, hydrophilic material in said chamber, said material swelling as it absorbs water and increasing its size and the girth of a penis in which the implant is implanted.

5. The implant of claim 4 in which the cover is made of an expandable material.

* * * * *